United States Patent [19]

Rao et al.

[11] 4,379,779

[45] Apr. 12, 1983

[54] EQUILIN HAPTEN AND ASSAY METHOD

[75] Inventors: Pemmaraju N. Rao; Robert H. Purdy; Perry H. Moore, Jr., all of San Antonio, Tex.

[73] Assignee: American Home Products Corporation, New York, N.Y.

[21] Appl. No.: 191,805

[22] Filed: Sep. 29, 1980

[51] Int. Cl.$^3$ .................... G01N 33/54; G01N 33/56; C07G 7/00; C07J 13/00
[52] U.S. Cl. ................................. 436/543; 260/112 B; 260/397.4; 260/397.5; 260/112 R; 436/804; 436/817; 436/822; 436/823
[58] Field of Search .............. 260/397.4, 397.5, 112 B; 424/1, 12; 23/230 B

[56] References Cited

U.S. PATENT DOCUMENTS 4,128,629 12/1978 Eldred et al. ............................ 424/1
4,293,536 10/1981 Jensen et al. ............................ 424/1

OTHER PUBLICATIONS

La Bella et al., Chem. Abstracts, vol. 90, 1979, Abstract #66958h.
Rance et al., J. Steroid Biochem., vol. 9, 1978, pp. 1065-1069.
Rao et al., Steroids, vol. 29, 1978, pp. 461-469.
Whittaker et al., Lancet, vol. 1, 1980, pp. 14-16.
Morgan et al., J. Steroid Biochem., vol. 13, 1980, pp. 551-555.
Johnson et al., J. Pharm. Sci., vol. 67, 1978, pp. 1218-1224.
Rao et al., Ligand Quarterly, vol. 3, No. 1, 1980, p. 53.

*Primary Examiner*—Christine M. Nucker
*Attorney, Agent, or Firm*—Arthur E. Wilfond

[57] ABSTRACT

A hapten is obtained by replacing the 3-hydroxy group of equilin with HO—CO—A—O— wherein A is an alkylene of one to six carbon atoms. The hapten is conjugated with an immunological carrier to provide an immunogen, which in turn produces a specific antiserum to equilin. The antiserum is used in a radioimmunoassay for equilin.

10 Claims, No Drawings

EQUILIN HAPTEN AND ASSAY METHOD

RELATED APPLICATION

A related application is P. N. Rao, U.S. Patent application Ser. No. 191,807, filed on the same day as this application.

BACKGROUND OF THE INVENTION

The present invention relates to an equilin hapten, to an immunogen for preparing an antiserum especially suited for use in the radioimmunoassay of equilin and to the antiserum. The invention also relates to a method of radioimmunoassay using the antiserum.

Equilin, in the form of its 3-sulfate salt, is a major component of conjugated (equine) estrogens which are used for the treatment of menopausal disorders. The three major components of conjugated (equine) estrogens by weight are estrone sulfate (about 50%), equilin sulfate (about 25%) and 17α-dihydroequilin 3-sulfate (about 15%). Although equilin is known to be a potent estrogen, little is known about its pharmacologic action and metabolism. A tool, which would be extremely useful to acquire knowledge about these parameters, would be a specific antiserum for equilin.

Specific antisera have been developed for such estrogens as estrone, 17β-estradiol and estriol, for example, see P. N. Rao and P. H. Moore, Jr., Steroids, 29, 461 (1977). An antiserum also has been reported for equilin, see P. G. Whittaker et al., The Lancet, 1, 14 (1980) and M. R. A. Morgan et at., J. Steroid Biochem., 13, 551 (1980); this antiserum is reported to have a cross reaction (4%) with the two major components of conjugated estrogens. A characteristic which distinguishes the latter antiserum from the present antiserum is that it is derived from an immunogen obtained by attaching a steroid to an immunological carrier by means of an ester linkage, a form of attachment different from that of the present immunogen. Notwithstanding these developments, a specific antiserum equilin would be of great value for determining equilin levels in plasma.

Accordingly, the present invention fulfills the above-noted need by providing a specific antiserum for the radioimmunoassay of equilin. The antiserum has a minimum of cross reaction with other steroids found in serum and/or steroids which form the conjugates present in conjugated estrogens.

SUMMARY OF THE INVENTION

The hapten of this invention is represented by formula I

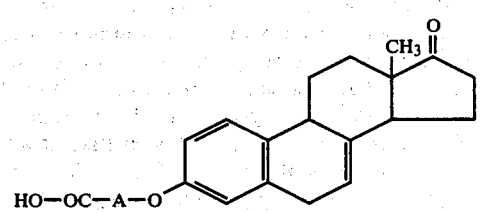

wherein A is an alkylene group of one to six carbon atoms.

The hapten can be used to prepare an immunogen and an antiserum. The antiserum is sufficiently specific to equilin in the presence of significant quantities of other steroids to enable a radioimmunoassay for equilin to be performed.

A preferred hapten is 3-hydroxy-1,3,5(10),7-estratetraen-17-one 3-O-carboxymethyl ether, i.e. the compound of formula I wherein A is methylene.

DETAILS OF THE INVENTION

The term "lower alkyl" as used herein means straight chain alkyl radicals containing from one to six carbon atoms and branched chain alkyl radicals containing from three to four carbon atoms, e.g. methyl, ethyl, propyl, 1-methylethyl, butyl, 1,1-dimethylethyl, pentyl and hexyl.

The term "alkylene" as used herein means a divalent organic radical derived from either a straight or branched chain aliphatic hydrocarbons, containing from one to six carbon atoms by removal of two hydrogen atoms, e.g. methylene, ethylene, 1-methylpropylene, 2-ethylpropylene and 2-butylethylene.

The terms "acyl" and "acylate" as used herein means straight chain 1-oxoalkyl radicals containing from one to ten carbon atoms and branched chain 1-oxoalkyl radicals containing from four to ten carbon atoms, e.g. formyl, acetyl, 1-oxopropyl, 1-oxobutyl, 2,2-dimethyl-1-oxopropyl, 1-oxohexyl and 1-oxo-3-ethyloctyl.

The term "lower alkoxy" as used herein means straight chain alkoxy radicals containing from one to six carbon atoms and branched chain alkoxy radicals containing three or four carbon atoms, e.g. methoxy, ethoxy, 1-methylethoxy, butoxy and hexanoxy.

The term "lower alkanol" as used herein means both straight and branched chain alkanols containing from one to four carbon atoms, e.g. methanol.

The term "halo" or "halogen" as used herein includes chlorine, bromine and iodine.

The term "organic proton acceptor" as used herein means the organic bases or amines, for instance, triethylamine, pyridine, N-ethylmorpholine and 1,5-diazabicyclo[4.3.0]non-5-ene.

The term "inorganic proton acceptor" as used herein means the inorganic bases, preferably the alkali methyl hydroxides, carbonates and bicarbonates; e.g. sodium bicarbonate and potassium carbonate.

The term "proton acceptor" as used herein means a proton acceptor selected from an organic proton acceptor and inorganic proton acceptor, as defined herein.

A convenient starting material to prepare the hapten of this invention is equilin, the preparation of which has been described several times; for example, see G. Kruger et al., U.S. Pat. No. 3,445,338, issued May 20, 1969.

Equilin also is known as 3-hydroxy-1,3,5(10),7-estratetraen-17-one.

The hapten of formula I can be prepared by reacting equilin with an ester of the formula $R^1OCO-A-X$ in which $R^1$ is lower alkyl, A is as defined herein and X is halo in the presence of an organic or inorganic proton acceptor to obtain the corresponding lower alkyl ester of the compound of formula I. Hydrolysis of the latter compound under alkaline conditions gives the desired hapten of formula I in which A is as defined herein.

In a preferred embodiment, equilin is reacted with an excess, for instance five to ten molar equivalents, of a lower alkyl ester of a haloacetic acid, preferably ethyl bromoacetate, in the presence of sodium or potassium carbonate in an inert solvent, for example, dimethylformamide, ethanol or acetone. In this manner, 3-hydroxy-1,3,5(10),7-estratetraen-17-one 3-O-(lower alkoxy)carbonylmethyl ether is obtained. The latter compound is hydrolyzed with an alkali metal salt of a lower alkanol in a solution of the lower alkanol, preferably sodium ethoxide in ethanol, to give the desired hapten of formula I in which A is methylene.

The hapten of this invention is capable, when linked to a suitable immunological carrier, preferably a protein, to produce an immunogen which can be employed in a host animal to elicit anti-equilin serum, specific to equilin. As used in this specification the term "immunogen" means a conjugate of a hapten and an immunological carrier, the immunogen being capable of causing an immunological response in a host animal. Amount such carriers are proteins, polymers, polysaccharides and polypeptides, all of which should have a molecular-weight of over 1000. The preferred carrier is bovine serum albumin (BSA); and other examples are the globulins, alpha-, beta-, gamma- and thyro-; and polylysine.

The conjugation of the instant hapten to the carrier can be done by procedures which are well known to those skilled in the art. Optionally, a coupling agent, for example a mixed anhydride, can be used.

The procedures for injecting the immunogen into a host animal and the recovery of the antibody are well known.

The antibody is employed in a radioimmunoassay for equilin. In accordance with such procedure, labeled steroid and unlabeled steroid present in a sample compete for binding sides on the antibody, and as a result of the competition, the ratio of bound labeled steroid to free labeled steroid diminishes as the concentration of unlabeled steroid in the sample increases. The amount of labeled steroid in a sample is obtained by comparing the inhibition observed with that produced by known amounts of unlabeled steroid, as presented in a standard curve. In this manner, a radioimmunoassay for detecting levels of 3-hydroxy-1,3,5(10),7-estratetraen-17-one (equilin) in a sample is provided employing radiolabeled 3-hydroxy-1,3,5(10),7-estratetraen-17-one and an antibody for binding 3-hydroxy-1,3,5(10),7-estratetraen-17-one and radiolabeled 3-hydroxy-1,3,5(10),7-estratetraen-17-one. The assay is characterized by employing the specific antibody of this invention.

The equilin may be present in the sample, either as the free compound itself or conjugated in the form of its 3-sulfate salt. When an assay of the amount of equilin 3-sulfate present in a serum sample is required, the sample first is extracted with a water immiscible solvent to remove the unconjugated steroids. Thereafter, the sample is subjected to mild acid hydrolysis to remove the sulfate portion from the conjugated steroid and provide the 3-hydroxy steroid, i.e. 3-hydroxy-1,3,5(10),7-estratetraen-17-one. It should be noted that in this instance standard hydrolysis techniques cause a considerable amount of aromatization to occur in the substrate steroid whereby the corresponding equilenin derivative is produced as a by-product. This transformation (aromatization) interferes with the assay of the steroid and, if not avoided, renders unreliable any assay method involving the conjugated form of equilin or an equilin derivative. A similar problem of the aromatization of equilin and 17α-dihydroequilin was reported in an earlier study by R. N. Johnson et al., J. Pharm. Sci. 67, 1218 (1978), and they did not find a satisfactory solution. This complication can be avoided by subjecting the sample of the conjugate to mild acid hydrolysis in the presence of a water soluble, non-protein binding antioxidant, for example, sulfur dioxide, chlorobutanol or preferably ascorbic acid. An additional requirement is that the antioxidant does not interfere with the assay procedure. In practice, convenient and efficient hydrolysis conditions include mixing the sample with an equal volume of a solution of formic acid (10 to 50%, v/v), ascorbic acid (0.1 to 1%, w/v) in an inert solvent, for example, ethyl acetate or a lower alkanol. Normally the duration of the reaction will depend on the temperature employed. Convenient times and temperatures for the hydrolysis are from one to six hours and 20°-60° C., respectively.

The following examples further illustrate this invention.

EXAMPLE 1

3-Hydroxy-1,3,5(10),7-estratetraen-17-one 3-O-ethoxycarbonylmethyl ether

To a solution of equilin (1.5 g, 5.6 mmol) in dry dimethylformamide (40 ml) was added anhydrous potassium carbonate (3.8 g, 28 mmol) and the mixture stirred under nitrogen for 15 min. Ethyl bromoacetate (3.6 ml, 33 mmol) was added and the mixture allowed to stir for 4 hours at room temperature, when thin layer chromatography (t.l.c.) in hexane-ethyl acetate (2:1, v/v) showed that the mixture no longer contained a detectable amount of equilin. The mixture was poured into ice water (400 ml) and extracted three times with diethyl ether (150 ml). After evaporation of the solvent in vacuo, the product was crystallized from aqueous ethanol to yield the title compound (1.75 g, 88%); m.p. 91.5°-92.5° C.; IR(KBr)1755, 1740, 1612, 1580, 1250 cm$^{-1}$; NMR(CDCl$_3$)δ0.75 (s, 18-CH$_3$), 1.30 (t,J=7, 5 Hz, -OCH$_2$CH$_3$), 3.15 (m, w$_{\frac{1}{2}}$=20 Hz, 9-H), 3.45 (m,w$_{\frac{1}{2}}$=11 Hz, 6-Hs), 4.27 (q, J=7.5 Hz, —O—CH$_2$CH$_3$), 4.60 (s, —OCH$_2$CO$_2$Et), 5.52 (br.s, 7-H), 6.67 (s, 4-H), 6.74 (d of d, J=8, 3 Hz, 2-H), 7.27 (d, J=8 Hz, 1-H)ppm; MS, m/e=354(M+); UV(CH$_3$OH) 278 nm (ε=1,760), 286 nm (ε=1,670).

EXAMPLE 2

3-Hydroxy-1,3,5(10),7-estratetraen-17-one 3-O-carboxymethyl ether

3-Hydroxy-1,3,5(10),7-estratetraen-17-one 30-ethoxycarbonylmethyl ether (0.6 g, 1.7 mmol, prepared as described in Example 1) was dissolved in dry methanol (100 ml) and a solution of sodium methoxide (0.201 g, 3,7 mmol, in 14 ml methanol was added. The mixture was refluxed under nitrogen for 4 hours, when t.l.c. in hexane-ethyl acetate (2:1, v/v) showed that the hydrolysis was about 90% complete. After cooling, the solvent was removed in vacuo and the residue partitioned between 100 ml of diethyl ether and water. The aqueous phase was acidified to pH 3 with 1N hydrochloric acid and the precipitate extracted with ethyl acetate (100 ml). The ethyl acetate was washed with water (50 ml) and evaporated in vacuo to yield the title compound (0.42 g, 76%); m.p. 183°-185° C. (after crystallization from acetone-hexane); IR(KBr) 1740, 1710, 1612, 1590, 1505, 1235 cm$^{-1}$; NMR (CD$_3$OD/acetone-d$_6$) δ 0.76 (s, 18-CH$_3$), 3.16 (m, w$_{\frac{1}{2}}$=20 Hz, 9-H), 3.45 (m, w$_{\frac{1}{2}}$=11 Hz, 6-Hs), 4.65 (s, -OCH$_2$CO$_2$H), 5.60 (br.s, 7-H), 6.67 (s, 4-H), 6.74 (d of d, J=8, 3 Hz, 2-H), 7.27 (d, J=8 Hz, 1-H)ppm; MS, m/e=326 (M=); UV(CH$_3$OH) 278 nm (ε=1,740), 286 nm (ε=1,640). Anal. Calc'd for C$_{20}$H$_{22}$O$_4$: C, 73.60; H, 6.79. Found: C, 73.33; H, 6.93.

EXAMPLE 3

Purification of [2,4-³H]-equilin by High Pressure Liquid Chromatography (HPLC)

Radioactive equilin was purchased from New England Nuclear Corporation, Boston, Mass. (Lot 853-278) with a specific activity of 41 Ci/mmol. It was purified by HPLC on a 0.96×50 cm preparative Chromegabond Diol column (E. S. Industries, Marlton, N.J., U.S.A.) using a gradient of 2.25 to 17.75% isopropanol in heptane over a 100 min period at a flow rate of 7.5 ml/min. Fractions were collected at one min intervals and a 50 μl aliquot of each fraction was analyzed for its content of ³H radioactivity. The ³H-labeled equilin was recovered as a single peak separated from the ³H-labeled impurity of equilenin.

EXAMPLE 4

Preparation of the steroid-bovine serum albumin conjugate and determination of the number of moles of steroid bound per mole of protein 3-Hydroxy-1,3,5(10),7-estratetraen-17-one 3-0-carboxylmethyl ether (0.5 mmol) was coupled to bovine serum albumin (BSA, 583 mg) by a mild procedure developed by U. Axen, Prostaglandins, 5, 45 (1974) using N,N'-carbonyldiimidazole, as reported by P. N. Rao and P. H. Moore, Jr., Steroids, 28, 101 (1976). Ultraviolet spectral analysis, see B. F. Erlanger et al., J. Biol. Chem., 228, 713 (1957), and determination of the free amino groups in the conjugate by a quantitative ninhydrin procedure, see S. Moor and W. H. Stein, J. Biol. Chem., 211 907 (1954), showed that the number of moles of steroid bound per mole of protein for equilin-BSA conjugate was 26 and 23, respectively.

EXAMPLE 5

Immunization Procedure and Collection of the Antibody

Five male New Zealand white rabbits, 4 months old, were used for immunization with each of the two different conjugates. The injection and bleeding schedules were exactly as reported by P. N. Rao and P. H. Moore, Jr., Steroids, 28, 101 (1976).

EXAMPLE 6

Assay Procedure

A standard was prepared from a stock solution of unlabeled equilin in absolute ethanol (100 ng/ml). A working standard solution containing 1 ng/ml of equilin was prepared in sodium phosphate buffer (0.1 M, pH 7, 0.9% NaCl). The labeled [2,4-³H]-equilin solution was prepared in the assay buffer at a concentration of 100 pg/ml. The antiserum was prepared in BSA-assay buffer (1 g BSA/1000 ml sodium phosphate buffer) at a concentration of one-fifth of the final working dilutions.

Plasma (0.2 ml) and distilled water (0.7 ml) were added to a 16×125 nm tube and mixed. [6,7-³H]-Estrone-3-sulfate (0.1 ml, 2,000 cpm) and [2,4-³H]-equilin (0.1 ml, 2,000 cpm) were then added to correct for recovery through the assay procedure, and the sample again mixed well and allowed to stand at room temperature for 30 min. Diethyl ether (2 ml) was added for extraction of the free compound. The extraction was repeated three times and the combined extracts washed with distilled water (1 ml) and the solvent removed by evaporation. The aqueous phase containing the conjugates was re-extracted with 2 ml of ethyl acetate-ethanol (4:1, v/v). The extraction was repeated two more times and the combined extracts were dried in a centrifuge tube (12 ml) under a stream of nitrogen. The conjugate fraction was hydrolyzed with formic acid. A solution of ethyl acetate (1 ml) containing formic acid (20%) and ascorbic acid (1 mg) was added to the tube containing the conjugate fraction. The tube was tightly closed, vortexed, and sonified for 10 min before being placed in a 37° C. water bath for 2 hr. The hydrolyzed sample was taken to dryness, sodium phosphate buffer (1 ml) was added. The solution was vortexed and allowed to stand at 20° C. for 10 min. The hydrolyzed free compound was extracted with diethyl ether (2 ml) three times and taken to dryness. Assay buffer (0.4 ml) was added to the sample tube and mixed. Aliquots of 0.1 ml were removed to count for recovery and 0.1 ml (2×) were removed for assay.

The standard curve was established by preparing duplicate 3 ml centrifuge tubes containing 0, 50, 100, 250, 500, 1000, and 2000 pg of equilin in a total volume of 0.5 ml assay buffer. The sample tubes were prepared in duplicate with hydrolyzed plasma extract (0.1 ml) and assay buffer (0.4 ml) in a total volume of 0.5 ml. To all standard and sample tubes antibody (0.25 ml) and labeled steroid (0.5 ml) were added. These were mixed and allowed to incubate at 4° C. for 18 hr. After addition of 0.2 ml gamma globulin dextrancoated charcoal (4 g charcoal, 0.4 g dextran, 0.8 g human gamma globulin, 200 ml deionized water), each tube was again mixed and placed in a cold room (4° C.) for 20 min. After centrifugation at 2,500 rev./min for 6 min, 0.5 ml of each supernatant was aliquoted into a counting vial. Then 15 ml of a scintillation medium (4 g of 2,5-diphenyloxazole (PPO), 50 mg of 1,4-di-2-(5-phenyloxazoyl)-benzene(dimethyl-POPOP), 100 ml of an aqueous solubilizer Biosolv BBS-3 (Biosolv is a trademark of Bechman Istruments, Irvine, Calif., U.S.A.) and 1000 ml toluene) was added to each vial. The samples were counted to a relative standard error of less than 2% in a Packard model 3320 liquid scintillation counter, Packard Instrument Co., Downers Grove, Ill., U.S.A., see C. Matthijssen and J. W. Goldzieher, Analyt. Biochem., 10, 401 (1965).

All rabbits immunized with the immunogen produced antisera with high titers and specificity in 6 months' time. The titer was determined from the ability of antibody to bind a constant amount (50 pg) of the labeled steroid. As a primary step, the cross-reactivity [G. E. Abraham, J. Clin. Endocrinol. Metabol., 29, 866 (1969)] of estrone with anti-equilin serum obtained from each rabbit was evaluated. This preliminary evaluation permitted the selection of the antiserum which exhibited the lowest cross-reactivity with sufficiently high titer and sensitivity for complete evaluation. The anti-equilin serum had a titer of 1:50,000 at 50% binding. The most significant observation was that this antiserum had negligible cross-reaction with estrone (Table 1) and exhibited only minor cross-reaction with equilenin (3.5%) and 17β-dihydroequilin (2.9%). These latter two compounds represent about 2% each of the typical composition of estrogens present in conjugated estrogens and will not interfere, as shown, in the validation of the assay. The binding affinity constant as determined by a Scatchard plot [G. Scatchard, Ann, N.Y. Acad. Sci., 51, 660 (1949)] was found to be $K_a = 3.4 = 10^9$ l./mol for the anti-equilin serum.

TABLE 1

Cross Reactivity Data

| Steroid | Equilin Antibody (Percent Cross-Reactivity) |
|---|---|
| Equilin | 100.0 |
| 17α-Dihydroequilin | <0.10 |
| Equilenin | 3.45 |
| 17β-Dihydroequilin | 2.86 |
| Equilin 3-Sulfate | 1.36 |
| 8-Dehydroestrone | 0.94 |
| Estrone | 0.78 |
| Estrone 3-sulfate | <0.10 |
| Equilin-7α,8α-glycol | <0.10 |
| 17α-Dihydroequilenin | <0.10 |
| 17β-Dihydroequilenin | <0.10 |
| 17α-Estradiol | <0.10 |
| 17β-Estradiol | <0.10 |
| 6-Dehydroestrone | <0.10 |
| 4-Androstene-3,17-dione | <0.10 |
| Androsterone | <0.10 |
| Dehydroepiandrosterone | <0.10 |
| Testosterone | <0.10 |
| Progesterone | <0.10 |
| Cortisol | <0.10 |

A study showed that during hydrolysis of the conjugate fraction with formic acid approximately 13–16% of equilin was oxidized to equilenin as evidenced by HPLC. In order to minimize this oxidation, 0.1% (w/v) ascorbic acid per sample was added to each sample before the hydrolysis with formic acid. By this procedure, the oxidation was minimized to 2–3%. In the actual assay procedure, no attempt was made to mathematically correct the final value due to the loss by oxidation. The overall recovery from plasma samples amounted to 72%.

In order to establish the usefulness of the antiserum in the actual radioimmunoassay, the following investigations were performed:

(1) a known amount of equilin was added to pooled female plasma and the level of the equilin in the plasma was determined by radioimmunoassay;

(2) increasing amounts of a standard mixture of free estrogens (Table 2), approximating the ratio of estrogens in conjugated estrogens, were added to plasma which already contained a known amount of equilin and the level of total equilin was determined; and (3) known amounts of equilin 3-sulfate were added to plasma in the presence of increasing amounts of conjugated estrogens and the levels of total equilin was determined after hydrolysis of the mixture of conjugates. The results of these investigations are presented in Tables 3 through 5.

TABLE 2

Composition of a standard mixture of unconjugated estrogen present in conjugated estrogens as the 3-sulfates.
Composition determined by gas liquid chromatography analysis

| STEROID | PERCENT |
|---|---|
| Estrone | 46.5 |
| Equilin | 25.6 |
| 17α-Dihydroequilin | 14.2 |
| 17α-Estradiol | 4.9 |
| Equilenin | 3.1 |
| 17α-Dihydroequilenin | 1.8 |
| 17β-Dihydroequilin | 1.72 |
| 8-Dehydroestrone | 1.51 |
| 17β-Dihydroequilenin | 0.42 |
| 17β-Estradiol | 0.26 |

TABLE 3

Recovery of equilin added to five 0.2 ml samples of pooled female plasma and measured in triplicate

| Estrogen added (ng) | Equilin Measured (ng)* | Recovery (%) | Coefficient of variation (%) |
|---|---|---|---|
| 0 | n.d.+ | — | — |
| 0.25 | 0.273 | 109 | 7 |
| 0.50 | 0.485 | 97 | 10 |
| 1.00 | 1.033 | 103 | 8 |

*Corrected for recovery of internal standard of [2,4-$^3$H]-equilin (average 69%).
+Not detectable.

TABLE 4

Recovery of equilin added as the reference standard, and/or in a standard mixture of unconjugated estrogens (Table 2), to five 0.2 ml samples of pooled female plasma and measured in duplicate

| Equilin added as reference standard (ng) | Equilin added in standard mixture (ng) | Equilin measured (ng)* | Difference (ng) | Coefficient of variation (%) |
|---|---|---|---|---|
| 0 | 0 | n.d.+ | — | — |
| 1.00 | 0 | 1.049 | 0.049 | 9 |
| 1.25 | 0 | 1.373 | 0.123 | 5 |
| 0 | 0.76 | 0.697 | −0.063 | 9 |
| 0.25 | 0.76 | 0.970 | −0.040 | 6 |
| 0 | 1.52 | 1.381 | −0.139 | 6 |
| 0.25 | 1.52 | 1.696 | −0.074 | 5 |

*Corrected for recovery of internal standard of [2,4-$^3$H] equilin (average 78%).
+Not detectable.

TABLE 5

Recovery of equilin from equilin 3-sulfate and conjugated estrogens added to five 0.2 ml samples of pooled female plasma and measured in duplicate

| ng Equilin added as the 3-sulfate | ng Equilin added in conjugated estrogens* | ng Equilin measured** | Difference (ng) | Coefficient of variation (%) |
|---|---|---|---|---|
| 0 | 0 | n.d.+ | — | — |
| 0.50 | 0 | 0.545 | 0.045 | 6 |
| 1.00 | 0 | 1.211 | 0.211 | 4 |
| 0 | 1.00 | 1.055 | 0.055 | 5 |
| 0.50 | 1.00 | 1.661 | 0.161 | 1 |
| 0 | 2.00 | 1.976 | −0.024 | 10 |
| 1.00 | 2.00 | 2.974 | −0.026 | 8 |

*Analyzed by gas liquid chromatography using the method of R. N. Johnson et al., cited above
**Corrected for recovery of internal standard of [6,7-$^3$H]-estrone 3-sulfate (average 65%).
+Not detectable.

The recovery of equilin from plasma (after correction for the recovery of the $^3$H-labeled internal standards) was essentially quantitative within the 6 to 10% coefficient of variation of the procedure. A total recovery of equilin from the standard mixture of estrogens (Table 4), or after hydrolysis of the mixture of sulfates (Table 5), was also achieved within the variability of the method.

In a study of plasma obtained from seven women 1 to 5 hours after thay had received conjugated estrogens, namely the brand sold under the trademark "Premarin", per os (0.625 to 2.5 mg), the average ratio of total equilin to total 17α-dihydroequilin was 1.83 (range 1.04 to 2.64); the 17α-dihydroequilin being assayed by the method described in copending U.S. Pat. application Ser. No. 191,807 filed of even date of the present application, and the equilin being filed by the present method. The ratio of these components in the conjugated estrogens is also 1.83; see R. N. Johnson et al., J. Pharm. Sci., 67, 1218 (1978). Only about 6% of the total level of equilin in these samples of plasma was present as the free compound; i.e. extractable with diethyl ether prior to hydrolysis. Since the hydrolysis procedure employed does not act on estrone 3-glucosiduronate, it is reasonable to assume that 94% of the total level of equilin was present in plasma as equilin 3-sulfate. This is in agreement with the well established fact that estrone 3-sulfate is the major circulating endogenous estrogen in humans, R. H. Purdy et al., J. Biol. Chem., 236, 1043 (1961); H. J. Ruder et al., J. Clin. Invest., 51, 1020 (1972); and C. Longcope and K. I. H. Williams, J. Clin. Endorinol. Metabol., 38, 602 (1974).

I claim:

1. A compound of the formula

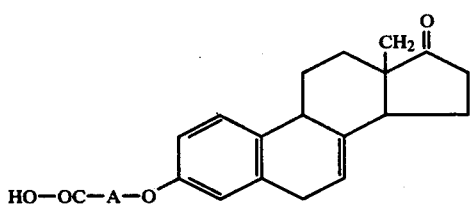

wherein A is an alkylene group of one to six carbon atoms.

2. 3-Hydroxy-1,3,5(10),7-estratetraen-17-one 3-O-carboxymethyl ether as claimed in claim 1.

3. An immunogen comprising the compound of claim 1 conjugated to an immunological carrier.

4. An immunogen comprising 3-hydroxy-1,3,5(10),7-estratetraen-17-one 3-O-carboxymethyl ether conjugated to an immunological carrier.

5. The immunogen of claim 4 wherein the carrier is bovine serum albumin.

6. The antibody produced by injecting the immunogen of claim 3 into a host animal.

7. The antibody produced by injecting the immunogen of claim 5 into a host animal.

8. In a radioimmunoassay procedure of 3-hydroxy-1,3,5(10),7-estratetraene-17-one in a sample employing radiolabeled 3-hydroxy-1,3,5(10),7-estratetraene-17-one and an antibody for binding 3-hydroxy-1,3,5(10),7-estratetraene-17-one and radiolabeled 3-hydroxy-1,3,5(10),7-estratetraene-17-one, the improvement which comprises employing the antibody of claim 6 or claim 7 in said radioimmunoassay procedure.

9. In a radioimmunoassay procedure of 3-hydroxy-1,3,5(10),7-estratetraen-17-one, wherein the sample for assay contains 3-hydroxy-1,3,5(10),7-estratetraen-17-one in the form of its 3-sulfate salt, the improvement which comprises subjecting the sample to hydrolysis conditions in the presence of a water soluble, non-protein binding antioxidant which does not interfere with the radioimmunoassay procedure.

10. In a radioimmunoassay procedure of 3-hydroxy-1,3,5(10),7-estratetraen-17-one, wherein the sample for assay contains 3-hydroxy-1,3,5(10),7-estratetraen-17-one in the form of its 3-sulfate salt, the improvement which comprises subjecting the sample to hydrolysis conditions in the presence of ascorbic acid.

UNITED STATES PATENT AND TRADEMARK OFFICE
CERTIFICATE OF CORRECTION

PATENT NO. : 4,379,779
DATED : April 12, 1983
INVENTOR(S) : Pemmaraju N. Rao

It is certified that error appears in the above-identified patent and that said Letters Patent is hereby corrected as shown below:

On the title page, item [75] should read as follows:

-- Inventor: Pemmaraju N. Rao

San Antonia, Texas --.

Signed and Sealed this

Sixteenth Day of August 1983

[SEAL]

*Attest:*

GERALD J. MOSSINGHOFF

*Attesting Officer*      *Commissioner of Patents and Trademarks*